United States Patent [19]

Matsui

[11] 4,443,195
[45] Apr. 17, 1984

[54] DRIVING AND WATER POURING CONTROL DEVICE FOR DENTAL AIR-TURBINE HANDPIECE

[75] Inventor: Takahiro Matsui, Uji, Japan

[73] Assignee: Kabushiki Kaisha Morita Seisakusho, Kyoto, Japan

[21] Appl. No.: 265,379

[22] Filed: May 20, 1981

[30] Foreign Application Priority Data

May 22, 1980 [JP] Japan .............................. 55-71100[U]
May 29, 1980 [JP] Japan .............................. 55-74923[U]

[51] Int. Cl.³ .............................................. A61C 1/08
[52] U.S. Cl. ....................................... 433/84; 433/98; 433/106; 251/63.4; 141/119
[58] Field of Search ................... 433/27, 28, 98, 106, 433/82, 84, 85, 86, 98, 99, 100; 251/30, 63.4, 139; 137/597; 141/119, 117, 116

[56] References Cited

U.S. PATENT DOCUMENTS

| | | | |
|---|---|---|---|
| 3,052,984 | 9/1962 | Mitthauer et al. | 433/106 |
| 3,069,776 | 12/1967 | Liedberg et al. | 433/27 |
| 3,106,021 | 10/1963 | Borden | 433/98 |
| 3,237,306 | 3/1966 | Staunt | 433/98 |
| 3,718,974 | 3/1973 | Buchtel et al. | 433/27 |
| 3,732,622 | 5/1973 | Rackson | 433/27 |
| 3,757,421 | 9/1973 | Kraft | 433/27 |
| 3,832,502 | 8/1974 | Grieger et al. | 251/63.4 |
| 3,902,247 | 9/1975 | Fleer et al. | 433/98 |
| 3,971,375 | 7/1976 | Hill | 433/98 |
| 3,991,473 | 11/1976 | Morgan | 433/28 |
| 4,069,587 | 1/1978 | Peralta | 433/28 |
| 4,136,450 | 1/1979 | Guenther et al. | 433/98 |
| 4,145,813 | 3/1979 | Hall | 433/98 |
| 4,173,827 | 11/1977 | Austin, Jr. | 433/98 |
| 4,185,385 | 1/1980 | Simor | 433/28 |
| 4,188,976 | 2/1980 | Austin, Jr. | 433/28 |
| 4,230,143 | 10/1980 | Dettmann et al. | 433/98 |
| 4,295,631 | 10/1981 | Allen | 251/30 |

FOREIGN PATENT DOCUMENTS 868247  5/1961  United Kingdom ................. 433/84

Primary Examiner—Gene Mancene
Assistant Examiner—David L. Tarnoff
Attorney, Agent, or Firm—Koda and Androlia

[57] ABSTRACT

This disclosure relates to a driving and water pouring control device for dental air-drive handpiece. According to the control device, there is incorporated a water pouring on-and-off valve means into an air feed passageway for driving a turbine so as to close and open the valve means by using part of air inside the passageway and to concurrently provide the valve means with a function of preventing water from dropping when pouring of water is stopped. The disclosure also relates to a device capable of compactly assembling therein device members.

4 Claims, 13 Drawing Figures

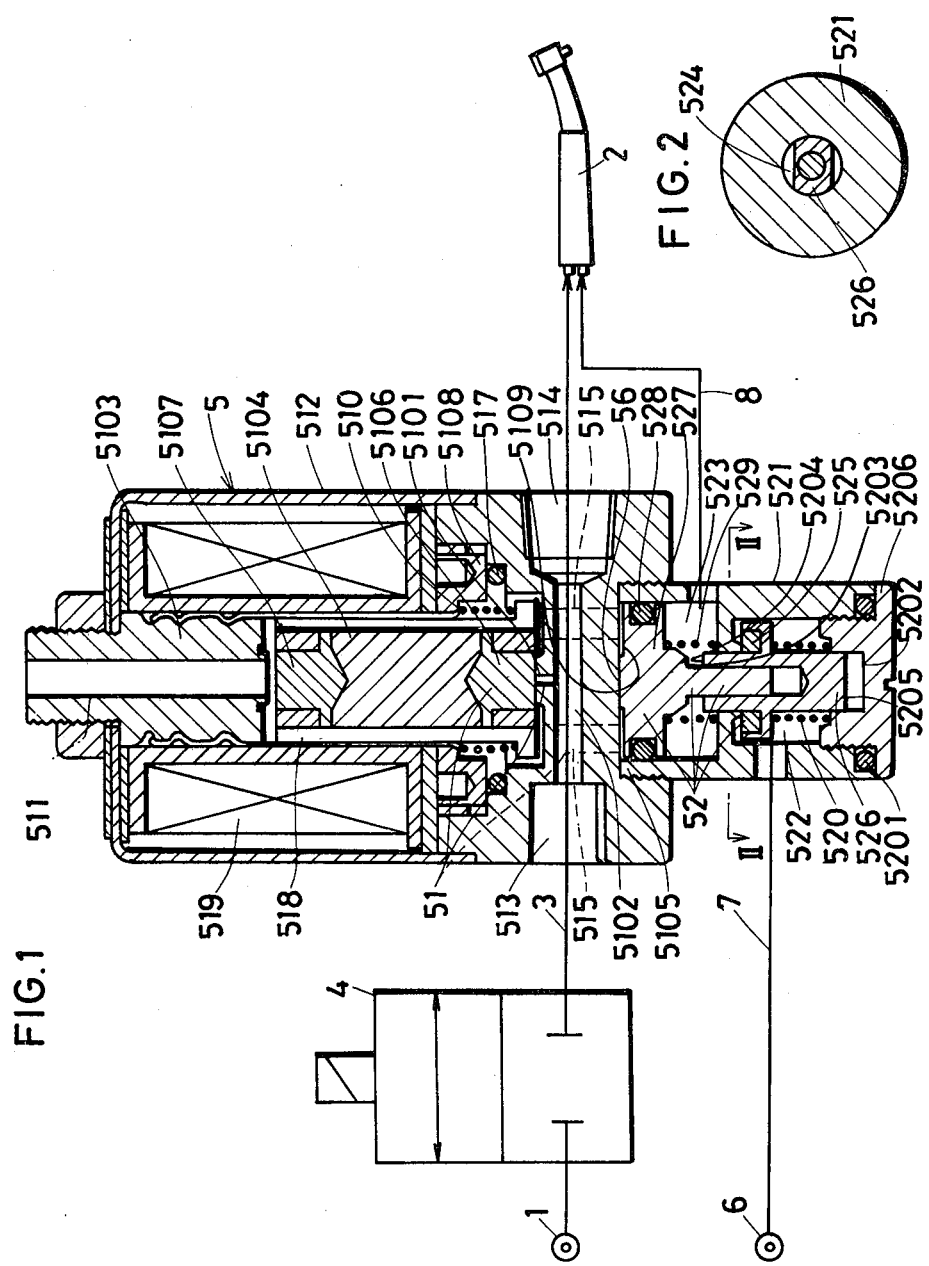

DRIVING AND WATER POURING CONTROL DEVICE FOR DENTAL AIR-TURBINE HANDPIECE

BACKGROUND OF THE INVENTION

1. Field of the Invention

This invention relates generally to a device for controlling driving and water pouring of dental handpiece and more particularly to a device for controlling driving and water pouring of dental handpiece, which device is intended to save power consumption of a solenoid valve itself by arranging an air path for driving an air-turbine and a water pouring path collectively in an operating path for one valve means through a newly provided water pouring on-and-off valve means and using part of air for driving the turbine as power for driving a piston of the water pouring on- and off valve means.

2. Prior Art

In conventional control devices for a dental air-turbine handpiece, a turbine driving valve means and a water pouring valve means for pouring water onto the front end of a handpiece tool were operated independently of each other, and even if no air was supplied, it was possible to pour water independently, with the result that power had to be supplied separately to solenoid valve means for operating the two valve means at the cost of economy. When the water pouring valve alone was operated when it was desired to supply water simultaneously with driving of the turbine, a patient has his clothes stained or part of pouring water permeated the handpiece not yet increased in inner pressure and formed a cause for engine trouble.

SUMMARY OF THE INVENTION

Accordingly, an object of the invention is to solve the problems described above. The object of the invention is achieved by incorporating a water pouring on-and-off valve means into an air feed passageway for driving a turbine, closing and opening the valve means by using part of air inside the passageway and concurrently providing the valve means with a function of preventing water from dropping when pouring of water is stopped.

Another object of the invention is to provide a device of the kind described above capable of compactly assembling therein device members.

According to the invention, power for operating the valve means for driving a turbine can be saved in comparision with the case in which when air is separately used for separate valve means for driving a turbine and for pouring water, and since pouring of water is possible only when the turbine starts driving, it is possible to prevent staining of patient's clothes and permeation of water through the blade unit which tend to occur when pouring of water alone is carried out because of malfunction.

A detailed description will now be given of preferred embodiments of the invention with reference to the accompanying drawings.

BRIEF EXPLANATION OF THE DRAWINGS

FIG. 1 is a longitudinal sectional front elevation showing the essential part of a first embodiment of the invention;

FIG. 2 is a sectional view taken along the line II—II of FIG. 1;

DETAILED DESCRIPTION OF THE PREFERRED EMBODIMENTS

Figure 3:
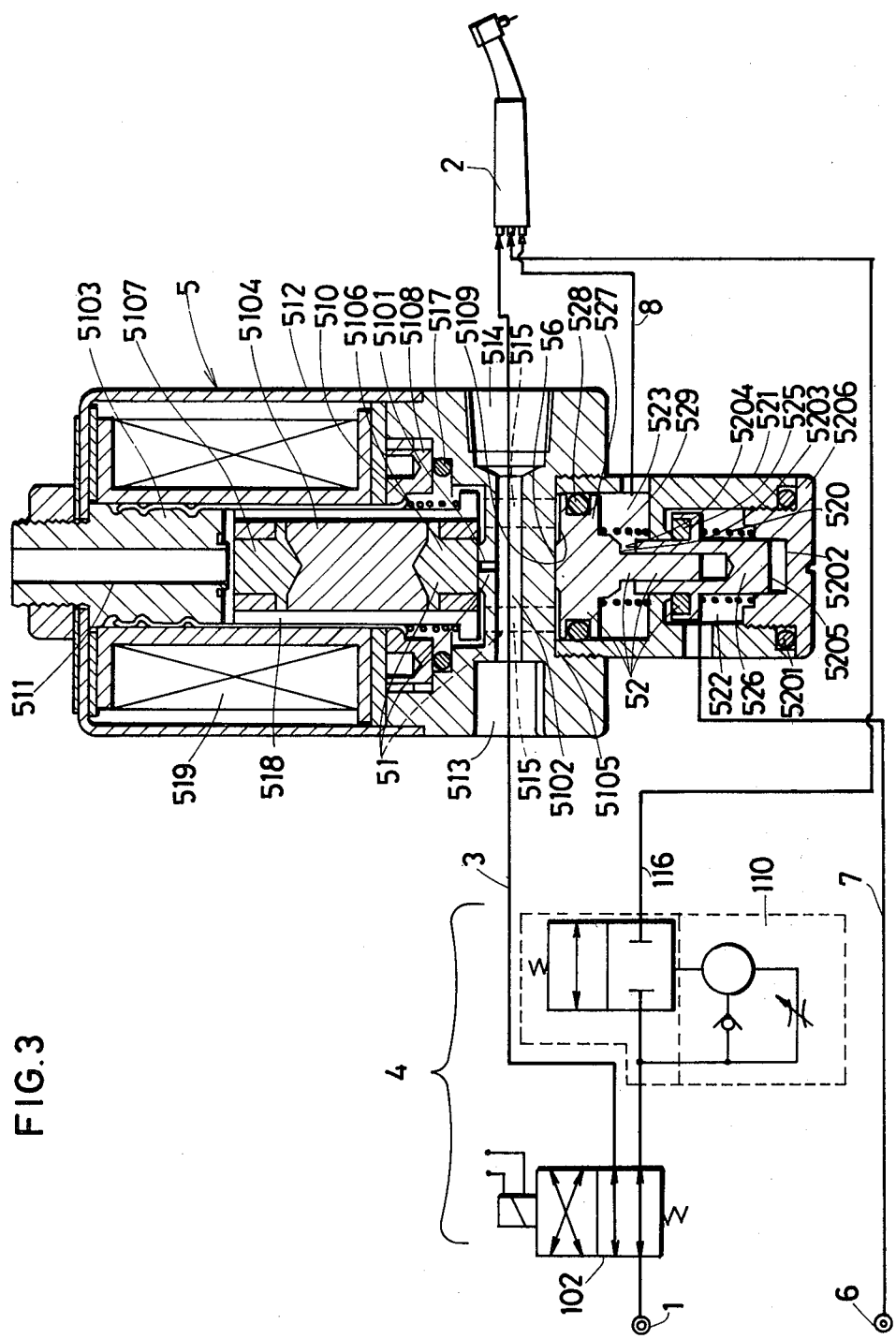
FIG. 3 is a longitudinal sectional front elevation showing the essential part of a second embodiment of the invention.

This invention is a driving and control device for dental air-turbine handpiece in which the device comprises an air supply on-and-off valve means 4 and a water pouring on-and-off valve means 5 disposed in their order midway in an air supply passageway 3 connecting a handpiece 2 to a compressed air source 1, a water pouring passageway 7 connecting the valve means 5 to the source 6, and a water pouring passageway 8 connecting the handpiece 2 to the valve means 5, the valve means 5 including a valve operating mechanism 51 and a valve mechanism 52, and the valve operating mechanism 51, when in its inoperative state, being brought into communication with the atmosphere through an air exhaust port 511 to thereby close the valve mechanism 52, but the mechanism 51, when in its operative state, closing the exhaust port 511 and introducing a part of compressed air from the air supply passageway 3 into the valve mechanism 52 to open the mechanism 52 and to thereby provide communication between water pouring passageways 7 and 8.

Four embodiments shown in FIGS. 1 to 5 are entirely the same in the water pouring on-and-off valve mechanism 5 but different in the air supply on-and-off valve means 4 in each embodiment. In the first embodiment is used a simple on-and-off control solenoid valve. In the second and third embodiments is used a valve means for enabling application of a sudden brake to a handpiece turbine when supply of air is stopped, and in the fourth embodiment is used a valve means for continuously changing a flow rate of air and optionally changing the driving characteristic of turbine when the valve means is turned on. The detail of the valve means 5 will later be described.

Referring now in detail to the water pouring on-and-off valve means 5, the means 5 is substantially the same in structure, work and effect as that in Japanese Utility Model Application No. 021014/1980 (filed on Feb. 19, 1980) filed previously by the applicant but is different from the water pouring on-and-off valve means in the prior application in design in which, when the means 5 is used in combination with an air supply passageway 3, the air in the passageway 3 may always pass through the means 5, namely the operating air for the means 5 may be supplied from a part of turbine driving air to the means 5 as long as the air supply on-and-off valve means 4 is on, and is structurally different in that an air exhaust port 514 is brought into communication with an air inlet port 513.

A detailed description will now be given of the water pouring on-and-off valve means 5 with reference to FIGS. 1 through 5. The numeral 521 designates a housing; 512 a four-way solenoid valve; 522 and 523 in the housing respectively designate airtightly formed water inlet and water outlet chambers respectively connected to a passageway 7 and a passageway 8; 524 a valve port for establishing communication between the chambers 522 and 523; and 526 designates a valve rod for fixing a valve body 525 positioned inside the water inlet chamber 522 and slidably passing through the valve port 524, the valve rod 526 being pressed by a spring 520 to normally close the valve port 524 by the valve body 525. The numeral 527 designates a piston which includes a sealer 528 and is positioned in the chamber 523 and which is designed to change the volume of the chamber 523 by movement of the piston. The four-way solenoid valve 512 is integrally connected to the housing 521 with screws and is sealed with a packing 5105. The numeral 56 designates an abutment face against which the piston 527 is normally pressed by a spring 529 so as to increase the chamber 523 to a maximum capacity. The air inlet port 513 connected to the air source 1 is in communication with an orifice 5101. The numeral 5104 designate a movable core having valve bodies 5106, 5107 at both ends and having a path 518 on the circumference thereof and which is pressed by a spring 510 to close the orifice 5101. The numeral 5103 designates a fixed core having an air exhaust port 511 which is connected to a four-way solenoid valve 512 through a pipe integral with the port 511 and through a screw member 5108 so as to make the valve 512 airtight with respect to the screw member 5108 through an O-ring 517. The numeral 519 designates an electromagnetic coil. In the embodiment illustrated, the orifice 5101 opening in the passageway 5102 connecting the air exhaust port 514 directly to the air inlet port 513 of the solenoid valve 512, a valve 5106, a passageway 518, an air exhaust port 511, an electromagnetic coil 519, a spring 510 and an air supply port 527 constitute a valve control unit 51, while a piston 527, springs 520, 529, a valve rod 526, a valve port 524 and a valve body 525 constitute a valve operating unit 52.

In the invention which comprises, in combination, the water pouring on-and-off valve means 5 of the structure described above and the air supply on-and-off valve means 4 which are interposed inside the passageway 3, when the means 4 is in off-position, compressed air is not supplied to the handpiece 2, but when the means 4 is turned on, air is continuously supplied to the handpiece 2 through the inlet port 513, passageway 5102, and air exhaust port 514 of the means 5. When the means 5 is in the state shown in FIGS. 1, 3, 4 and 5, namely when the electromagnetic coil 519 is not excited, the water supplied from the passageway 7 stays in the water inlet chamber 522 and the compressed air supplied to the passageway 5102 stays also in the passageway 5102 because the orifice 5101 is closed by the valve body 5106. When the coil 519 is excited, a movable core 5104 is attracted and moved toward a fixed core 5103 against the resilience of a spring 510 and closes an air exhaust port 511 with a valve body 5107 and opens an orifice 5101 to thereby permit supply of compressed air through an air supply port 515 to the air chamber 5109 disposed between a piston 527 and a four-way solenoid valve 512. The piston 527 is moved by the supply of compressed air to a valve rod 526 against the resilience of a spring 529 to bring one end 5204 of the valve rod 526 into contact with the face 5203 of the piston 527, presses the one end 5204 until the other end 5205 of the valve rod comes into contact with the concave surface 5202 of a cover 5206, whereupon closure of the valve port 524 with the valve body 525 is released to bring the water outlet chamber 523 into communication with the water inlet chamber 522, and water is poured from the nozzle of the handpiece 2 through the chambers 522, 523 and passageway 8 and a flexible connecting pipe (not shown).

When the electromagnetic coil 519 is de-excited, a movable core 5104 is returned by a spring 510 to its original position and closes the orifice 5101 with the valve body 5106 to shut off supply of compressed air and at the same time instantly discharges the compressed air in the air chamber 5109 between a four-way solenoid valve 512 and a piston 527 through an air supply port 515 and the passageway 518 from an opened air outlet port 511 into the atmosphere. By discharge of compressed air from the air chamber 5109, the valve rod 526 and the piston 527 are returned to their original state by the resilience of springs 520 and 529. At this time, the rod 526 and the piston 527 are moved together in the state of the surface 5203 of the piston 527 being in contact with the one end of the rod 526 until the valve rod 525 comes to the position in which the rod 525 closes the valve port 524. When the valve body 525 closes the valve port 524, supply of water from a water inlet chamber 522 to a water outlet chamber 523 is stopped. From this time onward, the piston 527 is further moved by the resilience of the spring 529 and stops only when the piston comes into contact with the abutment surface 56 of the solenoid valve 512. But since this successive movement of the piston 527 increases the capacity of the water outlet chamber 523 after supply of water has been cut, the pressure inside the chamber 523 is reduced to negative pressure and sucks water that tends to flow out from the nozzle of handpiece by contraction of the flexible connecting pipe to thereby prevent dropping of water from the handpiece nozzle. Also, even if the water inside the water outlet chamber 523 passes through the sealing portion of a sealing member 528 and enters the air supply port 515 of the solenoid valve 512 by movement of the piston 527, the water is discharged from an air exhaust port 518 together with compressed air when pouring of water is stopped, so that there is no possibility of the water staying in the solenoid valve 512 and permeating an electromagnetic coil 519 and hence no possibility of short-circuiting.

From the above, the invention makes it possible to pour water only when the handpiece 2 is driven by putting the air supply on-and-off valve means 4 into on-position, and accordingly, it is impossible to effect water pouring alone independently of the handpiece 2, with the result that there is no danger of mishandling of handpiece by an operator staining the clothes of a patient with dropped water or water improperly permeating the handpiece 2. In addition thereto, dropping of water from the tip of handpiece 2 is prevented by the means 5 itself. Another characteristic of the invention lies in the reduced number of valve members and in the reduction of power consumption for solenoid valve in that water pouring passageways 7 and 8 are bypassed through the means 4 to the turbine driving air supply passageway 3, namely, both passageways 3 and 7, 8 are collectively connected to an operating system of one valve without their being disposed in parallel with a separate valve mechanism.

Figure 4:
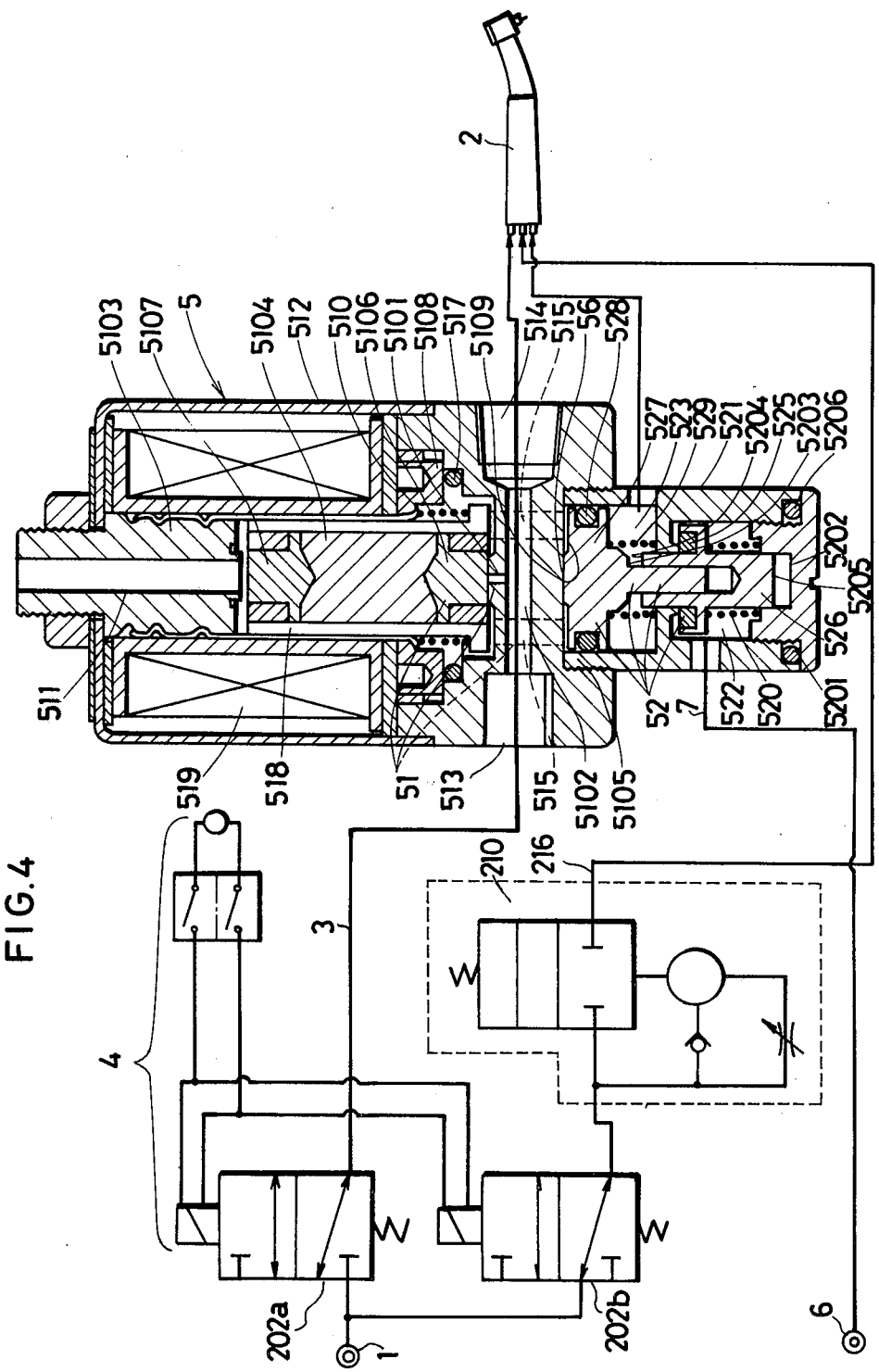
FIG. 4 is a longitudinal sectional front elevation showing the essential part of a third embodiment of the invention.
Figure 5:
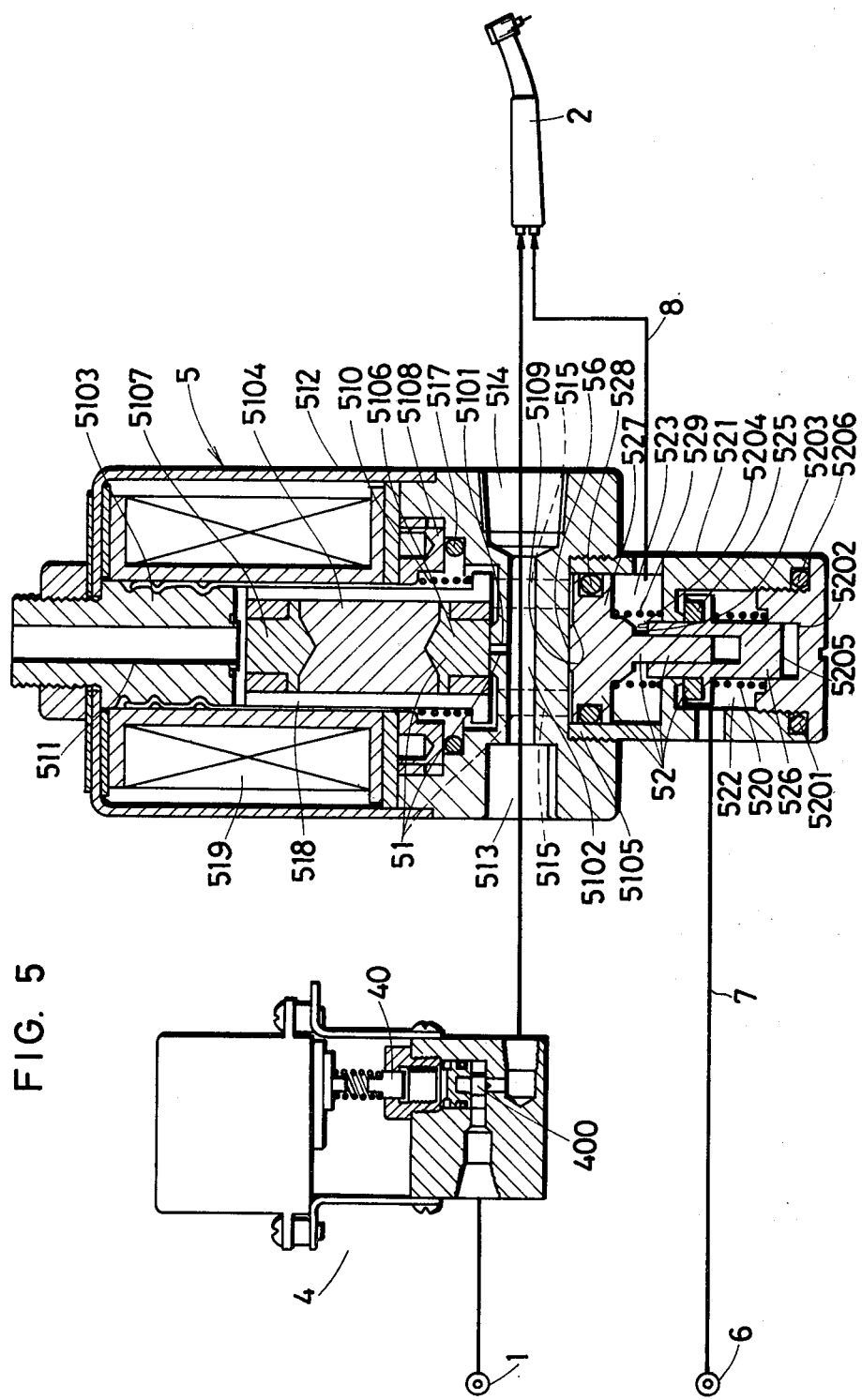
FIG. 5 is a longitudinal sectional front elevation showing the essential part of a fourth embodiment of the invention.

A first embodiment of the air supply on-and-off valve means 4 shown in FIG. 1 is shown in the form of an ordinary on-and-off solenoid valve means, but embodiment of the means 4 shown in FIGS. 3 and 4 are shown in the form of a solenoid valve means for bringing the handpiece 2 to a sudden stop by applying an air brake for stopping to the handpiece 2, and an embodiment in FIG. 5 is shown as a solenoid valve means for changing the driving characteristic of the turbine by electrically making automatic control of a flow rate of air to be supplied to the handpiece 2. Since a detailed description has been given of the solenoid valve means described above in Japanese Utility Model Application No. 021015/1980 (filed on Feb. 19, 1980) and Japanese Patent Application No. 020156/1980 (filed on Feb. 19, 1980) previously filed by the present applicant, a further description of the detail of the solenoid valve means is omitted. In short, in FIG. 3, a four-way solenoid valve 102 is used, and in FIG. 4, two three-way solenoid valves 202a and 202b which operate simultaneously in cooperation with each other are used. Both in the former valve 102 and in the latter valves 202a and 202b, after air supply through the valve 102 and through the valves 202a and 202b to the handpiece 2 has been stopped, compressed air is jetted from a passageway 116 or 216 from an opposite direction to thereby apply a brake to the turbine through changeover mechanisms 110, 210 inclusive of an air timer. Furthermore, the solenoid valve 102 or solenoid valves 202a and 202b are shown in their inoperative state in FIGS. 3 and 4. The solenoid valves shown in FIG. 5 controls a flow rate of air supply to the turbine of handpiece 2 by suitably making vertical movement of the valve rod 40 by a command signal from an electric circuit (not shown) to thereby make needle valve 400 free in its opening degree. The embodiments described above (shown in FIGS. 3, 4 and 5) provide greater convenience than the FIG. 1 embodiment in that a new function is added in the form of an air brake and air control. Although not shown, a combination of the second and fourth embodiments or of the third and fourth embodiments is also effective. Furthermore, it is also possible to use an air valve instead of the solenoid valve in the valve means 5.

As described, it will be understood that the invention is effective for eradicating the described disadvantage inherent in the prior art. The invention includes a compact structure that facilitates replacement of an air supply on-and-off valve means 4 in mounting the the valve means 4 and the water pouring on-and-off valve means 5 in conjunction with the air supply passageway 3 and water pouring passageway 7. Namely, the invention provides a mounting structure which is standardized to enable an ordinary user to simply and quickly replace the means 4 to be combined with the means 5 in assembling the control device of the kind described.

The object described is achieved by making the mounting structure detachable by a simple means of merely fixing the means 5 and means 4 through a support plate to a monostructure manifold body (as will presently be described) with locking means.

The structure of the kind described above will now be described in detail with reference to the accompanying drawings.

Figure 6:
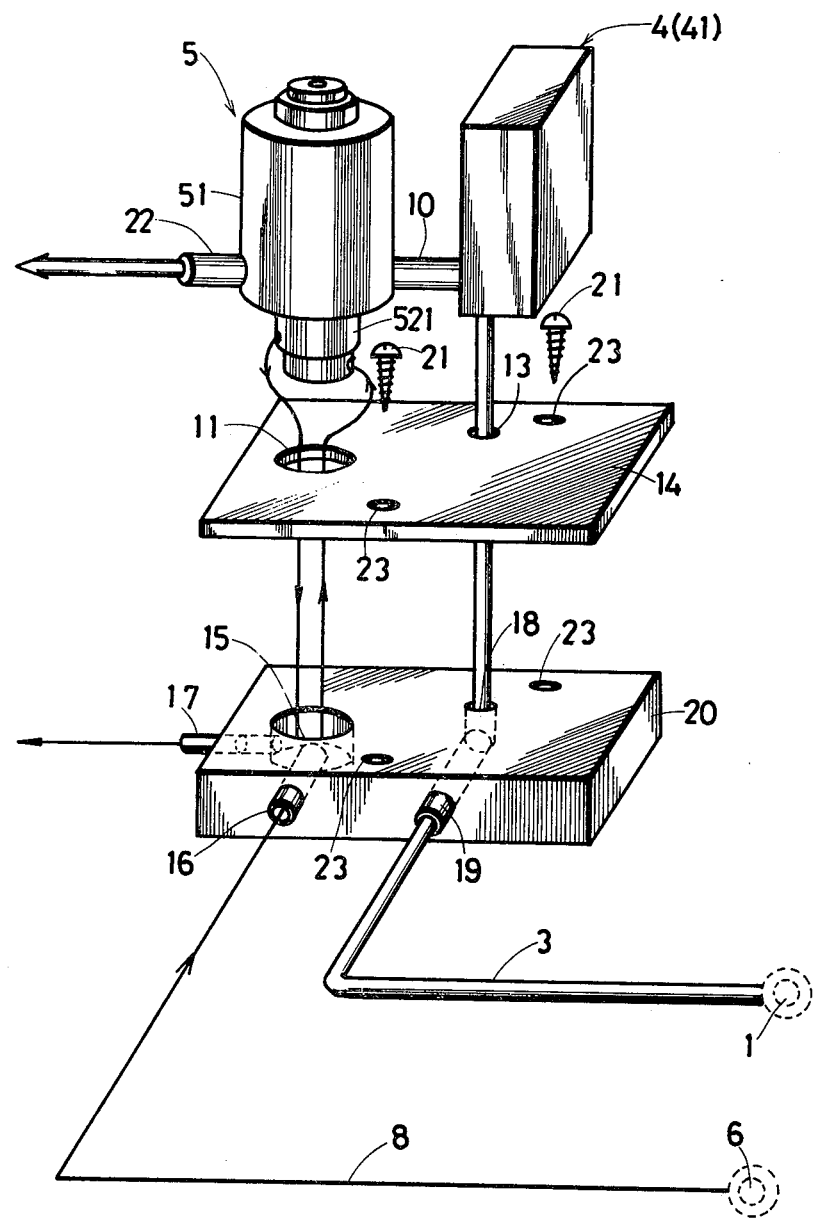
FIG. 6 is an exploded perspective view of the first embodiment showing an attachment structure of the device of the invention.

FIG. 6 is an exploded perspective view of the mounting structure described above and corresponding to the first embodiment of the invention. In the figure, the air inlet port 513 of the water pouring on-and-off valve means 5 is connected to the air supply on-and-off valve means 4 through a connecting pipe 10, and an air exhaust port 514 includes an air exhaust pipe 22 connected to an air supply pipe (not shown) of the handpiece h. The numeral 14 designates a support plate having a hole 11 for watertightly receiving thereinto a housing 521 provided under the water pouring on-and-off means 5, a hole 13 for airtightly receiving thereinto an air inlet port 12 (FIG. 7) in the air supply on-and-off valve means 4, and fitting holes 23, 23 for receiving locking means thereinto. The numeral 20 designates a manifold body, which includes a hole for watertightly receiving thereinto a housing 521 for the means 5 and a hole 18 for airtightly receiving thereinto the air inlet port 12 in the means 4. A water exhaust pipe 17 and a water introduction pipe 16 are brought into communication with an air supply pipe 19. The numerals 21 designate locking means for fixing the means 4 and the means 5 through the locking means fitting holes 23, 23 in the support plate 14 to the manifold body 20. The poured water exhaust pipe 17 of the manifold body 20 is connected to a water inlet port (not shown) for the handpiece h, the water introduction pipe 16 is connected to a water pouring passageway 8, and the air supply pipe 19 is connected to an air supply passageway 3.

Figure 7:
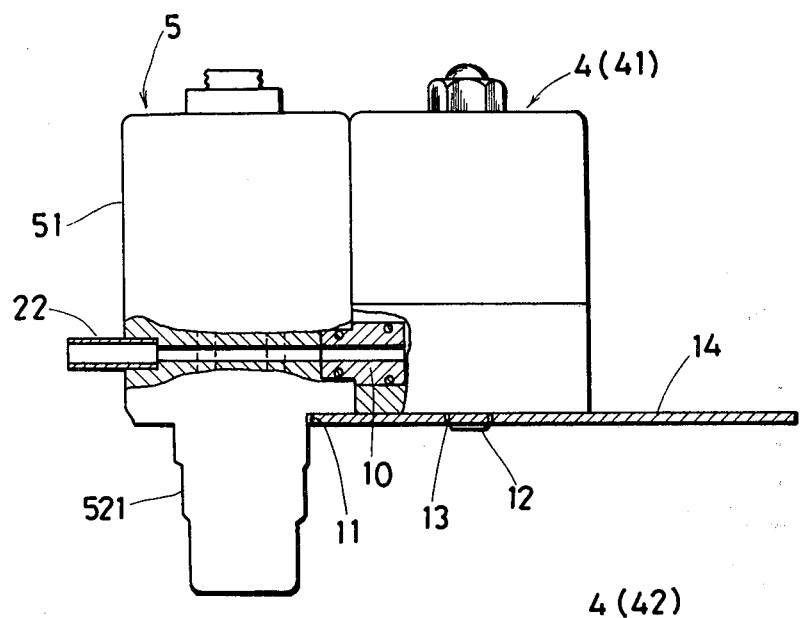
FIG. 7 is a segmentary longitudinal sectional front elevation showing the assembled state of the attachment structure of the invention.
Figure 8:
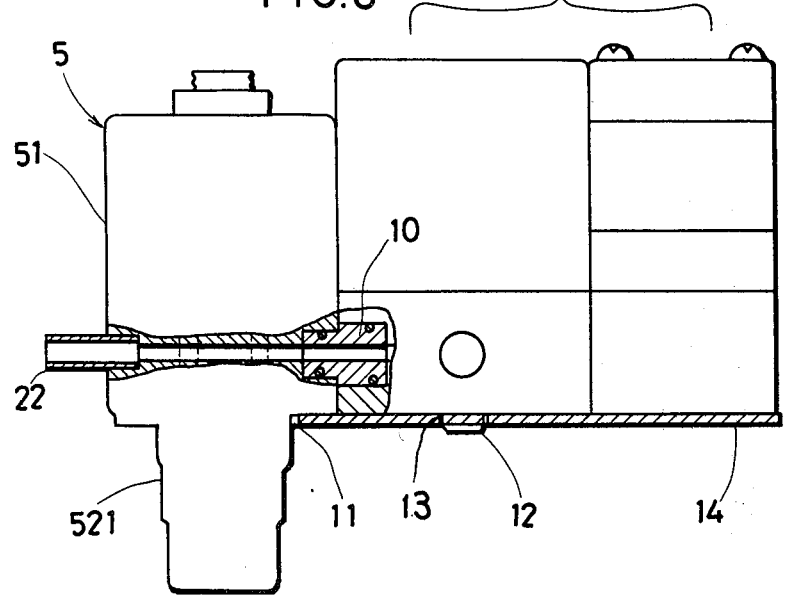
FIG. 8 is a segmentary longitudinal sectional front elevation similar to FIG. 7 and corresponding to the second and third embodiments of the invention.
Figure 9:
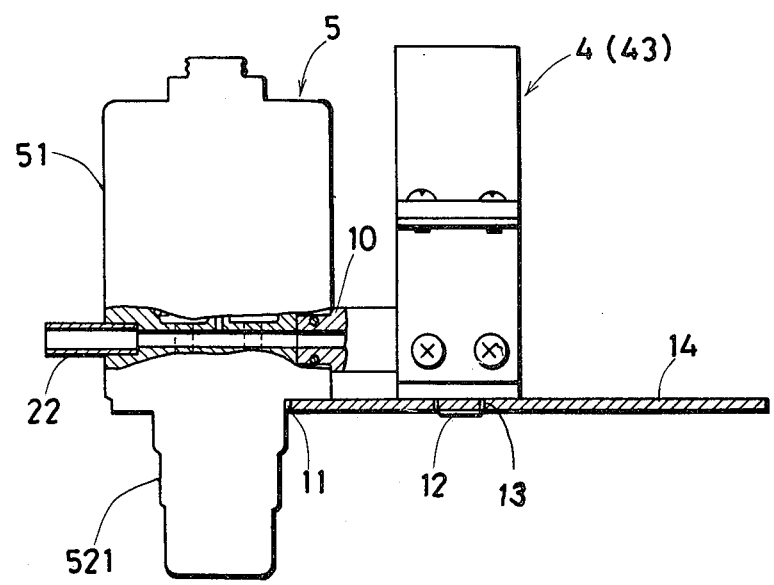
FIG. 9 is a segmentary longitudinal sectional front elevation similar to FIG. 7 and corresponding to the fourth embodiment.
Figure 10:
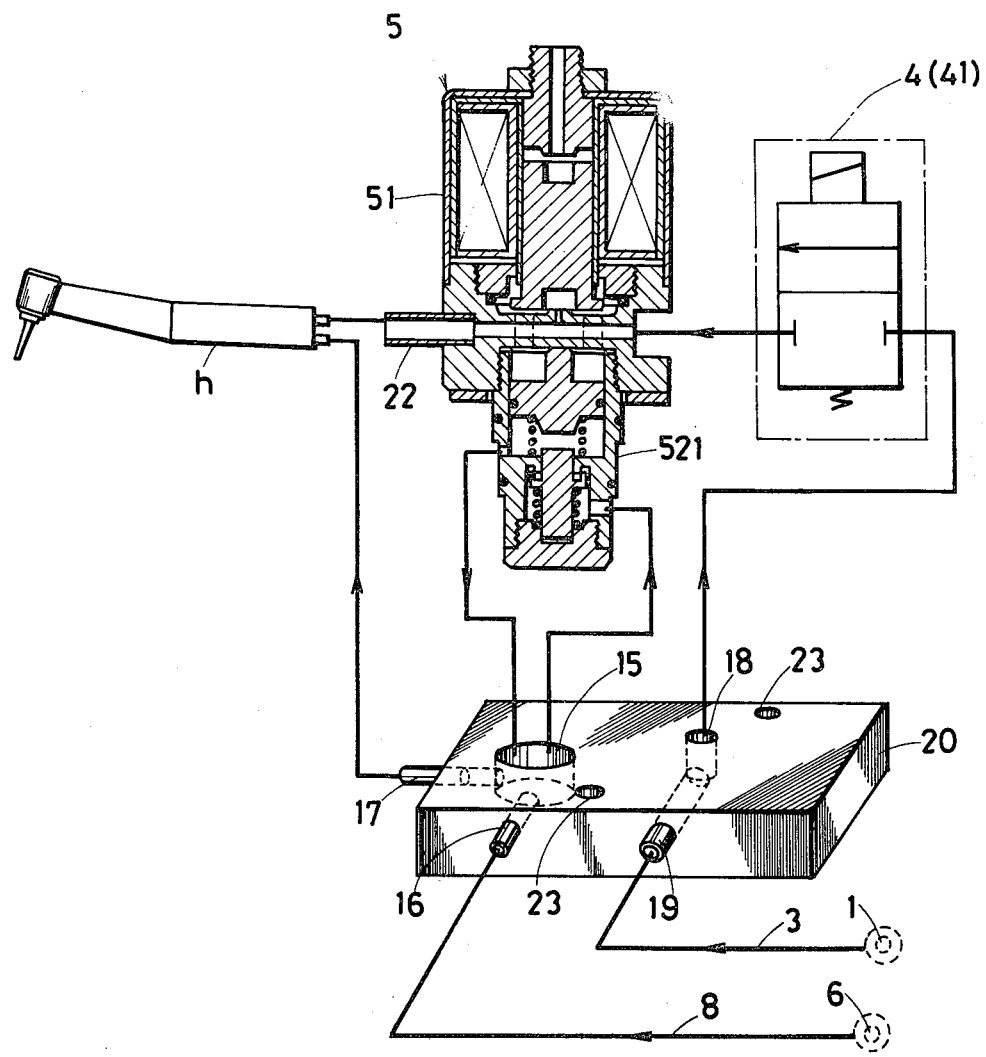
FIG. 10 is a schematic view illustrating the operating principle of the control device provided by the structure of FIG. 7.
Figure 11:
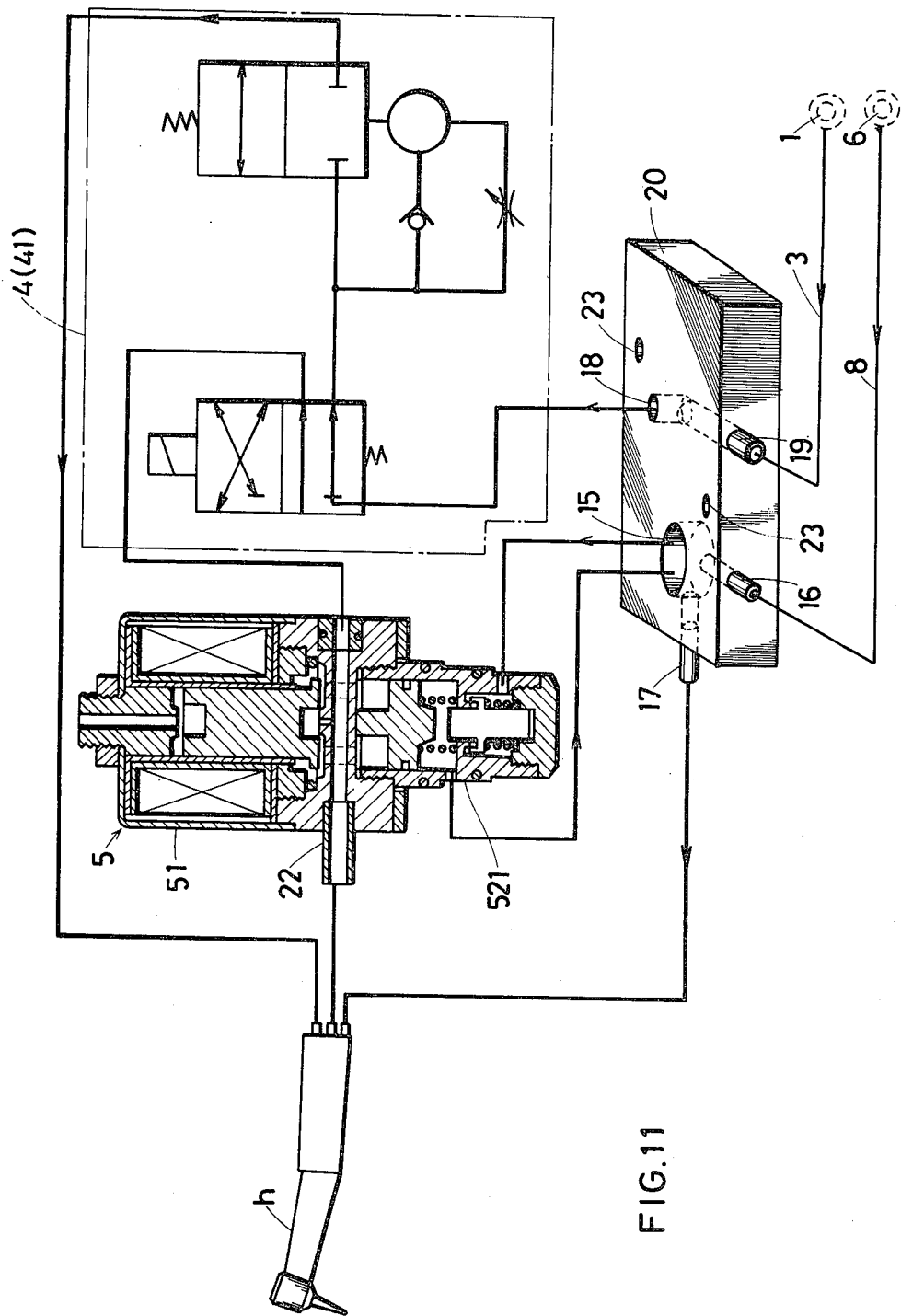
FIG. 11 is a view similar to FIG. 10 and corresponding to the structure of FIG. 8.
Figure 12:
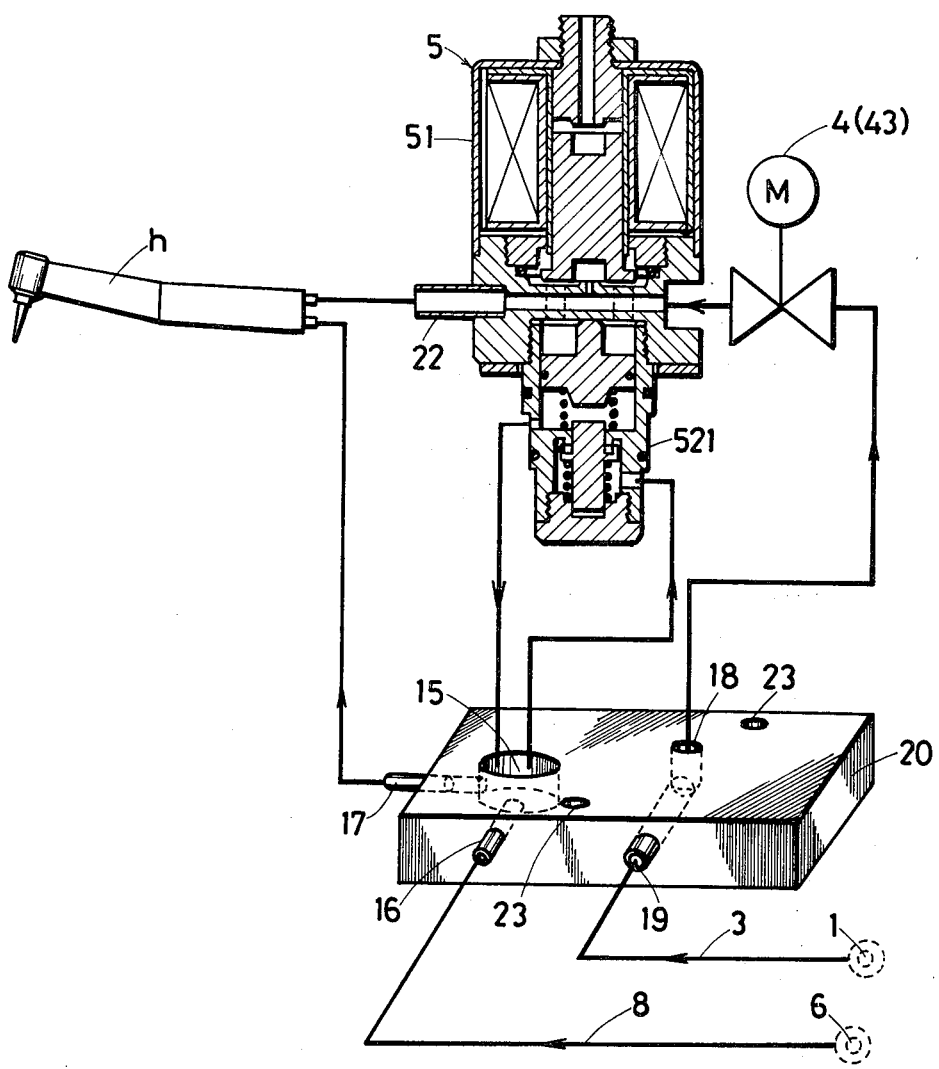
FIG. 12 is a view similar to FIG. 10 and corresponding to FIG. 9.

The device of the invention makes it possible to change the three kinds of control system described above easily and quickly by replacing the air supply on-and-off valve means 4 alone by causing the water pouring on-and-off valve means 5 to function concurrently as the means 4. Namely, for example, when the first embodiment control system is used as a control system for the control device, it is only necessary to construct the air supply on-and-off valve means 4 of an on-and-off solenoid valve 41 as shown in FIGS. 6 and 7, and when it becomes necessary to make sudden stop control by reverse rotation as shown in the second and third embodiments, all that is necessary is to construct the valve means 4 of an air valve means 42 as shown in FIG. 8 which enables the forced supply of air under pressure by which valve means 42 the handpiece is reversely rotated when driving of the handpiece is brought to a stop. When a variable speed control system as shown in the fourth embodiment is used, a motor valve 43 as shown in FIG. 9 may be used as the air supply on-and-off valve means 4. According to the invention, a control device is provided by air supply on-and-off valve means 41, 42 and 43 being beforehand connected in combination with the water pouring on-and-off valve means 5 and the combined valve means thus obtained being assembled into a manifold body 20 through the mentioned support plate 14 and being fixed with suitable locking means 21 . . . FIGS. 10 through 12 illustrate the operating principle of a control device attainable by the structure corresponding to FIGS. 7 through 9. As apparent from the figures, the invention makes it possible to relieve users of the trouble to disassemble and change control parts when a control system for handpiece h is changed, and makes it possible even for an ordinary dentist to change the control system by simple operation. According to the device of the invention, the number of handpieces is decreased and one handpiece provides various changes in control system with ease, and accordingly, the invention is useful for space saving and gives no inconvenience to dentists in their treatment activities.

Figure 13:
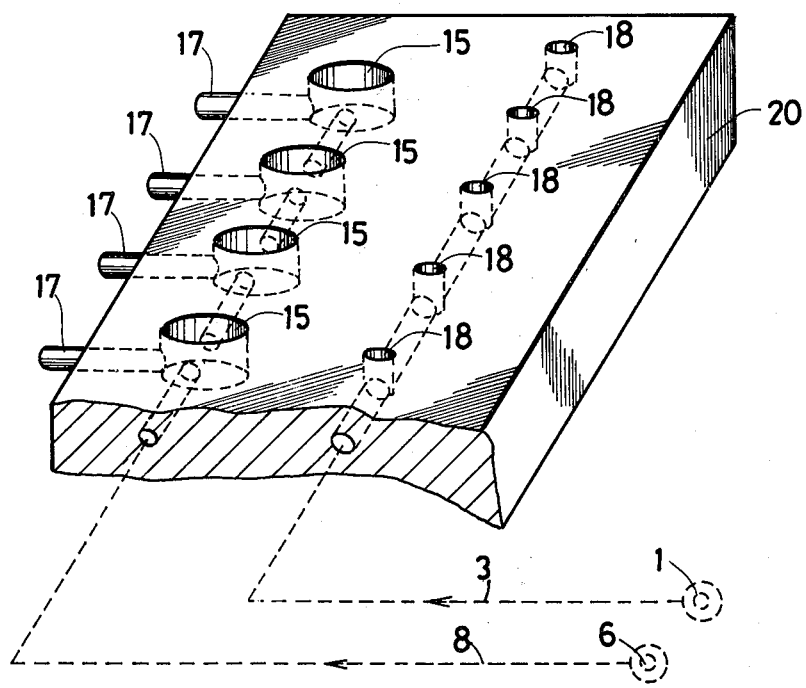
FIG. 13 is a perspective view, broken in part, of another embodiment of manifold body.

It is also possible from the structure described above to mount a plurality of water pouring on-and-off valve means 5 . . . and air supply on-and-off valve means . . . collectively in one manifold body 20. Namely, as shown in FIG. 13, a plurality of holes 15 . . . and holes 18 . . . are formed in one manifold body 20 to bring the respective holes 15 . . . and 18 . . . into communication with each other inside the manifold body 20, and if the holes 15 . . . and 18 . . . each are provided with valve means 5 . . . and 4 . . . through a support plate 14, integration of control devices is rendered possible, with the result that, when a plurality of handpieces are used, manipulation and maintenance of the handpieces are faciliated and simplified.

It should be understood that an air inlet port 12 of the air supply on-and-off valve means 4 may be provided in the form of an inlet pipe projecting at the lower end of the means 4 and a hole (not shown) corresponding thereto for tightly receiving the inlet pipe thereinto may be formed in the manifold body 20.

I claim:

1. A device for controlling driving and water pouring of a dental air-turbine handpiece, said device comprising an air supply on-and-off valve means and a water pouring on-and-off valve means disposed in an air supply passageway connecting a compressed air source to said handpiece, a first water pouring passageway connecting said water pouring valve means to a water source, and a second water pouring passageway connecting said handpiece to said water pouring valve means, said water pouring valve means including a valve control unit and a valve operating unit, said valve control unit, when in its inoperative state, communicating with the atmosphere through a first exhaust port to thereby close said valve operating unit, but said valve control unit, when in its operative state, closing said first air exhaust port and introducing part of said compressed air from said air supply passageway to the inside thereof to thereby open said valve operating unit so as to establish communication between said first and second water pouring passageways and wherein said water pouring on-and-off valve means comprises:

a four-way solenoid valve and a housing connected to said four-way solenoid valve, said four-way solenoid valve including a first air inlet port connected to said air supply passageway and a second air exhaust port communicating with said first inlet port, first air supply port and said first air exhaust port, said air exhaust port, when said first air inlet port is closed, communicating with said air supply port, said first air inlet port, when said first air exhaust port is closed, communicating with said air supply port, said housing including a water inlet chamber connected to said first water pouring passageway and a water outlet chamber connected to said second water pouring passageway, said water inlet and outlet chambers both communicating with each other through a valve port, said port having a valve rod passing therethrough, said valve rod having a valve body fixed thereto and adapted to close said valve port, said water outlet chamber incorporating thereinto a piston, said piston being normally pressed against the abutment surface of said solenoid valve and being moved toward said valve rod by compressed air supplied from said air supply port of said solenoid valve and thereafter being driven to further press against said valve rod so as to open the valve port closed by said valve body; and wherein said air supply on-and-off valve means further comprises:

an air inlet port at the lower end thereof, said housing of said water pouring on-and-off valve means projecting downwardly of a valve controlling unit, the air exhaust side of said air supply on-and-off valve means being connected by a connecting pipe to the air inlet port of said water pouring on-and-off valve means, a support member including a first hole for watertightly receiving said housing thereinto and a second hole for airtightly receiving said air inlet port thereinto, a water introduction pipe and a water discharge pipe communicating with said first hole, and an air supply pipe communicating with said second hole which is disposed on a lower side of said water pouring and air supply on-and-off valve means, said housing and said air inlet port resting in said first and second holes respectively and said pouring passageway and said air supply passageway being respectively connected to said water introduction pipe and to said air supply pipe.

2. A device according to claim 1 wherein said air supply on-and-off valve means includes a function capable of applying an air brake to a handpiece for some time after having cut off air supply.

3. A device according to claim 1 wherein said air supply on-and-off valve means includes a function capable of changing a flow rate of air supply to handpiece.

4. A device according to claim 1 wherein a plurarity of first and second holes are provided in said support member, each of said first and second holes respectively communicating with each other inside said support member, a plurality of air supply on-and-off valve means and water pouring on-and-off valve means being each provided in one of said first and second holes so as to generally provide a plurality of valve means collectively in one support member.

* * * * *